(12) United States Patent
Dandekar et al.

(10) Patent No.: US 7,297,829 B2
(45) Date of Patent: Nov. 20, 2007

(54) AROMATICS ALKYLATION

(75) Inventors: Ajit B. Dandekar, South Plainfield, NJ (US); John P. McWilliams, Woolwich Township, NJ (US); Thomas Francis Degnan, Moorestown, NJ (US); Michael Hryniszak, Bordentown, NJ (US); Donald J. Klocke, Somerdale, NJ (US); Wieslaw Jerzy Roth, Sewell, NJ (US)

(73) Assignee: ExxonMobil Chemical Patents Inc., Houston, TX (US)

( * ) Notice: Subject to any disclaimer, the term of this patent is extended or adjusted under 35 U.S.C. 154(b) by 159 days.

(21) Appl. No.: 11/128,721

(22) Filed: May 13, 2005

(65) Prior Publication Data

US 2005/0209493 A1  Sep. 22, 2005

Related U.S. Application Data

(63) Continuation of application No. 09/845,856, filed on Apr. 30, 2001, now Pat. No. 7,038,100.

(51) Int. Cl.
*C07C 2/66* (2006.01)
(52) U.S. Cl. ..................................... 585/467
(58) Field of Classification Search ........... 585/467; 502/55, 38
See application file for complete search history.

(56) References Cited

U.S. PATENT DOCUMENTS

| | | | |
|---|---|---|---|
| 3,766,093 A | 10/1973 | Chu | 252/455 Z |
| 3,894,104 A | 7/1975 | Chang et al. | 260/668 R |
| 3,962,364 A | 6/1976 | Young | 260/671 C |
| 4,288,647 A | 9/1981 | Chu | 585/467 |
| 4,356,338 A | 10/1982 | Young | 585/407 |
| 4,439,409 A | 3/1984 | Puppe et al. | 423/328 |
| 4,463,209 A * | 7/1984 | Kursewicz et al. | 585/467 |
| 4,518,703 A | 5/1985 | Young | 502/63 |
| 4,668,837 A | 5/1987 | Dianis | 585/466 |
| 4,826,667 A | 5/1989 | Zones et al. | 423/277 |
| 4,891,458 A | 1/1990 | Innes et al. | 585/323 |
| 4,954,324 A | 9/1990 | Hooper | 423/239 |
| 4,962,256 A | 10/1990 | Le et al. | 585/467 |
| 4,992,606 A | 2/1991 | Kushnerick et al. | 585/467 |
| 5,110,776 A | 5/1992 | Chitnis et al. | 502/64 |
| 5,231,064 A | 7/1993 | Absil et al. | 502/68 |
| 5,236,575 A | 8/1993 | Bennett et al. | 208/46 |
| 5,243,116 A | 9/1993 | Lee et al. | 585/467 |
| 5,250,277 A | 10/1993 | Kresge et al. | 423/329.1 |
| 5,362,697 A | 11/1994 | Fung et al. | 502/71 |
| 5,371,310 A | 12/1994 | Bennett et al. | 585/467 |
| 5,401,896 A | 3/1995 | Kuehl et al. | 585/455 |
| 5,453,554 A | 9/1995 | Cheng et al. | 585/467 |
| 5,470,810 A | 11/1995 | Degnan et al. | 502/64 |
| 5,488,194 A | 1/1996 | Beck et al. | 585/475 |
| 5,493,065 A * | 2/1996 | Cheng et al. | 585/467 |
| 5,536,894 A | 7/1996 | Degnan et al. | 585/467 |
| 5,557,024 A | 9/1996 | Cheng et al. | 585/467 |
| 5,939,597 A | 8/1999 | Dessau et al. | 585/447 |

* cited by examiner

*Primary Examiner*—Thuan Dinh Dang
(74) *Attorney, Agent, or Firm*—Darryl M. Tyus; Xiaobing Feng

(57) ABSTRACT

The present invention provides a process for producing an alkylaromatic compound comprising the step of contacting an alkylatable aromatic compound with an alkylating agent under alkylation conditions in the presence of a alkylation catalyst comprising phosphorus and a porous crystalline inorganic oxide material having an X-ray diffraction pattern including the d-spacing maxima at 12.4±0.25, 6.9±0.15, 3.57±0.07 and 3.42±0.07 Angstrom.

6 Claims, No Drawings

AROMATICS ALKYLATION

This application is a continuation of U.S. application Ser. No. 09/845,856, filed Apr. 30, 2001 and now U.S. Patent No. 7,038,100.

BACKGROUND OF THE INVENTION

The present invention relates to aromatics alkylation, and in particular to the alkylation of benzene with ethylene and propylene to produce ethylbenzene and cumene, respectively. In addition, the invention is concerned with the alkylation of aromatics with long chain ($C_6$+) alkylating agents to produce long chain alkylbenzenes.

Ethylbenzene and cumene are valuable commodity chemicals which are used industrially for the production of styrene monomer and phenol, respectively. In addition, long chain alkylbenzenes are useful as lubricant base stocks and as intermediates in the production of detergents.

Alkylation is one of the most important and useful reactions of hydrocarbons. Lewis and Bronsted acids, including a variety of natural and synthetic zeolites, have been used as alkylation catalysts. Alkylation of aromatic hydrocarbon compounds employing certain crystalline zeolite catalysts is known in the art. In particular, alkylation of benzene with ethylene and propylene in the presence of zeolite catalysts represents the preferred commercial techniques for the production of ethylbenzene and cumene.

For example, U.S. Pat. No. 4,992,606 describes the use of MCM-22 in the alkylation of aromatic compounds, such as benzene, with alkylating agents having aliphatic groups with 1 to 5 carbon atoms, such as ethylene and propylene. Similarly, U.S. Pat. No. 4,962,256 describes the use of MCM-22 in the alkylation of aromatic compounds with alkylating agents having aliphatic groups with at least 6 carbon atoms.

The use of MCM-49 in the alkylation of aromatic compounds with short chain alkylating agents is described in U.S. Pat. No. 5,371,310 and in alkylation of aromatic compounds with long chain alkylating agents is described in U.S. Pat. No. 5,401,896.

The use of MCM-56 in the alkylation of aromatic compounds with short chain alkylating agents is described in U.S. Pat. Nos. 5,453,554 and 5,557,024.

It is also known from U.S. Pat. No. 5,470,810 that the addition of phosphorus to MCM-22 improves the hydrothermal stability of the resulting catalyst for use in catalytic cracking.

U.S. Pat. No. 3,962,364 discloses that the addition of at least 0.5 wt % phosphorus to a zeolite having a constraint index of 1-12, in particular ZSM-5, increases the selectivity of the zeolite in the vapor phase alkylation of aromatic hydrocarbons with olefins.

According to the invention, it has now been found that modification of MCM-22 and certain related molecular sieve catalysts, such as MCM-49 and MCM-56, with phosphorus increases the activity of the catalyst for the alkylation of aromatic compounds. In addition, the phosphorus modification increases the selectivity of the catalyst towards the monoalkylated product and enhances its stability against the hydrothermal deactivation which can occur during regeneration.

SUMMARY OF THE INVENTION

According to the invention, there is provided a process for producing an alkylaromatic compound comprising the step of contacting an alkylatable aromatic compound with an alkylating agent under alkylation conditions in the presence of an alkylation catalyst comprising phosphorus and a porous crystalline inorganic oxide material having an X-ray diffraction pattern including the d-spacing maxima at 12.4±0.25, 6.9±0.15, 3.57±0.07 and 3.42±0.07 Angstrom.

Preferably, the porous crystalline inorganic oxide material is selected from the group consisting of MCM-22, PSH-3, SSZ-25, MCM-36, MCM-49 and MCM-56.

Preferably, the alkylating agent has an aliphatic group having 1 to 5 carbon atoms.

Preferably, the aromatic hydrocarbon is benzene and the alkylating agent is selected from ethylene and propylene.

Preferably, said alkylation conditions are such as to maintain said alkylatable aromatic compound substantially in the liquid phase.

DETAILED DESCRIPTION OF THE INVENTION

The present invention relates to a process for the production of an alkylaromatic compound, particularly ethylbenzene or cumene, by the alkylation of an alkylatable aromatic compound, particularly benzene, with an alkylating agent, particularly ethylene or propylene, under alkylation conditions with a phosphorus-containing porous crystalline inorganic oxide material having an X-ray diffraction pattern including the d-spacing maxima at 12.4±0.25, 6.9±0.15, 3.57±0.07 and 3.42±0.07 Angstrom.

The term "aromatic" in reference to the alkylatable compounds which are useful herein is to be understood in accordance with its art-recognized scope which includes alkyl substituted and unsubstituted mono- and polynuclear compounds. Compounds of an aromatic character which possess a hetero atom are also useful provided they do not act as catalyst poisons under the reaction conditions selected.

Substituted aromatic compounds which can be alkylated herein must possess at least one hydrogen atom directly bonded to the aromatic nucleus. The aromatic rings can be substituted with one or more alkyl, aryl, alkaryl, alkoxy, aryloxy, cycloalkyl, halide, and/or other groups which do not interfere with the alkylation reaction.

Suitable aromatic hydrocarbons include benzene, naphthalene, anthracene, naphthacene, perylene, coronene, and phenanthrene, with benzene being preferred.

Generally the alkyl groups which can be present as substituents on the aromatic compound contain from 1 to about 22 carbon atoms and usually from about 1 to 8 carbon atoms, and most usually from about 1 to 4 carbon atoms.

Suitable alkyl substituted aromatic compounds include toluene, xylene, isopropylbenzene, normal propylbenzene, alpha-methylnaphthalene, ethylbenzene, cumene, mesitylene, durene, p-cymene, butylbenzene, pseudocumene, o-diethylbenzene, m-diethylbenzene, p-diethylbenzene, isoamylbenzene, isohexylbenzene, pentaethylbenzene, pentamethylbenzene; 1,2,3,4-tetraethylbenzene; 1,2,3,5-tetramethylbenzene; 1,2,4-triethylbenzene; 1,2,3-trimethylbenzene, m-butyltoluene; p-butyltoluene; 3,5-diethyltoluene; o-ethyltoluene; p-ethyltoluene; m-propyltoluene; 4-ethyl-m-xylene; dimethylnaphthalene; ethylnaphthalene; 2,3-dimethylanthracene; 9-ethylanthracene; 2-methylanthracene; o-methylanthracene; 9,10-dimethylphenanthrene; and 3-methyl-phenanthrene. Higher molecular weight alkylaromatic hydrocarbons can also be used as starting materials and include aromatic hydrocarbons such as are produced by the alkylation of aromatic hydrocarbons with olefin oligomers. Such products are frequently referred to in the art as alkylate and include hexylbenzene, nonylbenzene, dodecylbenzene, pentadecylbenzene, hexyltoluene, nonyltoluene, dodecyltoluene and pentadecyltoluene. Very often alkylate is obtained as a high boiling fraction in which the alkyl group attached to the aromatic nucleus varies in size from about $C_6$ to about $C_{12}$. When cumene or ethylbenzene is the desired product, the present process produces acceptably little by-products such as xylenes. The xylenes make in such instances may be less than about 500 ppm.

Reformate containing substantial quantities of benzene, toluene and/or xylene constitutes a particularly useful feed for the alkylation process of this invention.

The alkylating agents which are useful in the process of this invention generally include any aliphatic or aromatic organic compound having one or more available alkylating aliphatic groups capable of reaction with the alkylatable aromatic compound.

Preferably, the alkylating agent employed herein has at least one alkylating aliphatic group possessing from 1 to 5 carbon atoms. Examples of such alkylating agents are olefins such as ethylene, propylene, the butenes, and the pentenes; alcohols (inclusive of monoalcohols, dialcohols and trialcohols) such as methanol, ethanol, the propanols, the butanols, and the pentanols; aldehydes such as formaldehyde, acetaldehyde, propionaldehyde, butyraldehyde, and n-valeraldehyde; and alkyl halides such as methyl chloride, ethyl chloride, the propyl chlorides, the butyl chlorides and the pentyl chlorides.

Mixtures of light olefins are especially useful as alkylating agents in the alkylation process of this invention. Accordingly, mixtures of ethylene, propylene, butenes, and/or pentenes which are major constituents of a variety of refinery streams, e.g., fuel gas, gas plant off-gas containing ethylene, propylene, etc., naphtha cracker off-gas containing light olefins and refinery FCC propane/propylene streams, are useful alkylating agents herein. For example, a typical FCC light olefin stream possesses the following composition:

|  | Wt. % | Mole % |
| --- | --- | --- |
| Ethane | 3.3 | 5.1 |
| Ethylene | 0.7 | 1.2 |
| Propane | 4.5 | 15.3 |
| Propylene | 42.5 | 46.8 |
| Isobutane | 12.9 | 10.3 |
| n-Butane | 3.3 | 2.6 |
| Butenes | 22.1 | 18.32 |
| Pentanes | 0.7 | 0.4 |

Reaction products which may be obtained from the process of the invention using short chain ($C_1$-$C_5$) alkylating agents include ethylbenzene from the reaction of benzene with ethylene, cumene from the reaction of benzene with propylene, ethyltoluene from the reaction of toluene with ethylene, cymenes from the reaction of toluene with propylene, and sec-butylbenzene from the reaction of benzene and n-butenes.

Alternatively, the alkylating agent used in the process of the invention has one or more alkylating aliphatic groups with at least about 6 carbon atoms, preferably at least about 8, and still more preferably at least about 12 carbon atoms. Examples of suitable long chain alkylating agents are olefins such as hexenes, heptenes, octenes, nonenes, decenes, undecenes and dodecenes; alcohols (inclusive of monoalcohols, dialcohols, and trialcohols) such as hexanols, heptanols, octanols, nonanols, decanols, undecanols and dodecanols; and alkyl halides such as hexyl chlorides, octyl chlorides, dodecyl chlorides; and, higher homologs of the foregoing. Branched alkylating agents, especially oligomerized olefins such as the trimers, tetramers and pentamers, of light olefins, such as ethylene, propylene and butylenes, are also useful herein.

The alkylation catalyst used in the process of the invention comprises phosphorus and a porous crystalline inorganic oxide material having an X-ray diffraction pattern including d-spacing maxima at 12.4±0.25, 6.9±0.15, 3.57±0.07 and 3.42±0.07 Angstrom. The X-ray diffraction data used throughout this specification were obtained by standard techniques using the K-alpha doublet of copper as the incident radiation and a diffractometer equipped with a scintillation counter and associated computer as the collection system.

Suitable porous crystalline inorganic oxide materials are MCM-22 (described in U.S. Pat. No. 4,954,325), PSH-3 (described in U.S. Pat. No. 4,439,409), SSZ-25 (described in U.S. Pat. No. 4,826,667), MCM-36 (described in U.S. Pat. No. 5,250,277), MCM-49 (described in U.S. Pat. No. 5,236,575) and MCM-56 (described in U.S. Pat. No. 5,362,697). All the above U.S. patents are incorporated herein by reference.

The alkylation catalyst used in the process of the invention also contains phosphorus. The amount of phosphorus, as measured on an elemental basis, may be between about 0.05 and about 10 wt. %, preferably between about 0.1 and about 2 wt. %, and most preferably between about 0.1 and about 0.5 wt. %, based on the weight of the final catalyst.

Incorporation of the phosphorus modifier into the catalyst of the invention is conveniently achieved by the methods described in U.S. Pat. Nos. 4,356,338, 5,110,776 and 5,231,064, the entire disclosures of which are incorporated herein by reference. Treatment with phosphorus-containing compounds can readily be accomplished by contacting the porous crystalline material, either alone or in combination with a binder or matrix material, with a solution of an appropriate phosphorus compound, followed by drying and calcining to convert the phosphorus to its oxide form. Contact with the phosphorus-containing compound is generally conducted at a temperature of about 25° C. and about 125° C. for a time between about 15 minutes and about 20 hours. The concentration of the phosphorus in the contact mixture may be between about 0.01 and about 30 wt. %.

Representative phosphorus-containing compounds which may be used include derivatives of groups represented by $PX_3$, $RPX_2$, $R_2PX$, $R_3P$, $X_3PO$, $(XO)_3PO$, $(XO)_3P$, $R_3P{=}O$, $R_3P{=}S$, $RPO_2$, $RPS_2$, $RP(O)(OX)_2$, $RP(S)(SX)_2$, $R_2P(O)OX$, $R_2P(S)SX$, $RP(OX)_2$, $RP(SX)_2$, $ROP(OX)_2$, $RSP(SX)_2$, $(RS)_2PSP(SR)_2$, and $(RO)_2POP(OR)_2$, where R is an alkyl or aryl, such as phenyl radical, and X is hydrogen, R, or halide. These compounds include primary, $RPH_2$, secondary, $R_2PH$, and tertiary, $R_3P$, phosphines such as butyl phosphine, the tertiary phosphine oxides, $R_3PO$, such as tributyl phosphine oxide, the tertiary phosphine sulfides, $R_3PS$, the primary, $RP(O)(OX)_2$, and secondary, $R_2P(O)OX$, phosphonic acids such as benzene phosphonic acid, the corresponding sulfur derivatives such as $RP(S)(SX)_2$ and $R_2P(S)SX$, the esters of the phosphonic acids such as dialkyl phosphonate, $(RO)_2P(O)H$, dialkyl alkyl phosphonates, $(RO)_2P(O)R$, and alkyl dialkylphosphinates, $(RO)P(O)R_2$; phosphinous acids, $R_2POX$, such as diethylphosphinous acid, primary, $(RO)P(OX)_2$, secondary, $(RO)_2POX$, and tertiary, $(RO)_3P$, phosphites, and esters thereof such as the monopropyl ester, alkyl dialkylphosphinites, $(RO)PR_2$, and dialkyl alkyphosphinites, $(RO)_2PR$. Corresponding sulfur derivatives may also be employed including $(RS)_2P(S)H$, $(RS)_2P(S)R$, $(RS)P(S)R_2$, $R_2PSX$, $(RS)P(SX)_2$, $(RS)_2PSX$, $(RS)_3P$, $(RS)PR_2$, and $(RS)_2PR$. Examples of phosphite esters include trimethylphosphite, triethylphosphite, diisopropylphosphite, butylphosphite, and pyrophosphites such as tetraethylpyrophosphite. The alkyl groups in the mentioned compounds preferably contain one to four carbon atoms.

Other suitable phosphorus-containing compounds include ammonium hydrogen phosphate, the phosphorus halides such as phosphorus trichloride, bromide, and iodide, alkyl phosphorodichloridites, (RO)PCl$_2$, dialkylphosphorochloridites, (RO)$_2$PCl, dialkylphosphinochloridites, R$_2$PCl, alkyl alkylphosphonochloridates, (RO)(R)P(O)Cl, dialkyl phosphinochloridates, R$_2$P(O)Cl, and RP(O)Cl$_2$. Applicable corresponding sulfur derivatives include (RS)PCl$_2$, (RS)$_2$PCl, (RS)(R)P(S)Cl, and R$_2$P(S)Cl.

Particular phosphorus-containing compounds include ammonium phosphate, ammonium dihydrogen phosphate, diammonium hydrogen phosphate, diphenyl phosphine chloride, trimethylphosphite, phosphorus trichloride, phosphoric acid, phenyl phosphine oxychloride, trimethylphosphate, diphenyl phosphinous acid, diphenyl phosphinic acid, diethylchlorothiophosphate, methyl acid phosphate, and other alcohol-P$_2$O$_5$ reaction products.

After contacting with the phosphorus-containing compound, the catalyst may be dried and calcined to convert the phosphorus to an oxide form. Calcination can be carried out in an inert atmosphere or in the presence of oxygen, for example, in air at a temperature of about 150 to 750° C., preferably about 300 to 500° C., for at least 1 hour, preferably 3-5 hours.

The porous crystalline oxide material employed in the alkylation catalyst of the invention may be combined with a variety of binder or matrix materials resistant to the temperatures and other conditions employed in the process. Such materials include active and inactive materials such as clays, silica and/or metal oxides such as alumina. The latter may be either naturally occurring or in the form of gelatinous precipitates or gels including mixtures of silica and metal oxides. Use of a material which is active, tends to change the conversion and/or selectivity of the catalyst and hence is generally not preferred. Inactive materials suitably serve as diluents to control the amount of conversion in a given process so that products can be obtained in an economical and orderly manner without employing other means for controlling the rate of reaction. These materials may be incorporated into naturally occurring clays, e.g., bentonite and kaolin, to improve the crush strength of the catalyst under commercial operating conditions. Said materials, i.e., clays, oxides, etc., function as binders for the catalyst. It is desirable to provide a catalyst having good crush strength because in commercial use it is desirable to prevent the catalyst from breaking down into powder-like materials. These clay and/or oxide binders have been employed normally only for the purpose of improving the crush strength of the catalyst.

Naturally occurring clays which can be composited with the porous crystalline material include the montmorillonite and kaolin family, which families include the subbentonites, and the kaolins commonly known as Dixie, McNamee, Georgia and Florida clays or others in which the main mineral constituent is halloysite, kaolinite, dickite, nacrite, or anauxite. Such clays can be used in the raw state as originally mined or initially subjected to calcination, acid treatment or chemical modification.

In addition to the foregoing materials, the porous crystalline material can be composited with a porous matrix material such as silica-alumina, silica-magnesia, silica-zirconia, silica-thoria, silica-beryllia, silica-titania as well as ternary compositions such as silica-alumina-thoria, silica-alumina-zirconia silica-alumina-magnesia and silica-magnesia-zirconia.

The relative proportions of zeolite and inorganic oxide matrix vary widely, with the content of the former ranging from about 1 to about 90% by weight and more usually, particularly when the composite is prepared in the form of beads, in the range of about 2 to about 80 wt. % of the composite.

The alkylation process of this invention is conducted such that the organic reactants, i.e., the alkylatable aromatic compound and the alkylating agent, are brought into contact with an alkylation catalyst in a suitable reaction zone such as, for example, in a flow reactor containing a fixed bed of the catalyst composition, under effective alkylation conditions. Such conditions include a temperature of from about 0C to about 500° C., and preferably between about 50° C. and about 250° C., a pressure of from about 0.2 to about 250 atmospheres, and preferably from about 5 to about 100 atmospheres, a molar ratio of alkylatable aromatic compound to alkylating agent of from about 0.1:1 to about 50:1, and preferably can be from about 0.5:1 to about 10:1, and a feed weight hourly space velocity (WHSV) of between about 0.1 and 500 hr$^{-1}$, preferably between 0.5 and 100 hr$^{-1}$.

The reactants can be in either the vapor phase or the liquid phase and can be neat, i.e., free from intentional admixture or dilution with other material, or they can be brought into contact with the zeolite catalyst composition with the aid of carrier gases or diluents such as, for example, hydrogen or nitrogen. Preferably, the alkylation conditions are such as to maintain the alkylatable aromatic compound substantially in the liquid phase. For example, the alkylation reaction can be conducted by reactive distillation.

When benzene is alkylated with ethylene to produce ethylbenzene, the preferred catalyst is phosphorus-modified MCM-22 and alkylation reaction is preferably carried out in the liquid phase. Suitable liquid phase conditions include a temperature between 300° F. and 600° F. (about 150° C. and 316° C.), preferably between 400° F. and 500° F. (about 205° C. and 260° C.), a pressure up to about 3000 psig (20875 kPa), preferably between 400 and 800 psig (2860 and 5600 kPa), a space velocity between about 0.1 and 20 WHSV, preferably between 1 and 6 WHSV, based on the ethylene feed, and a ratio of the benzene to the ethylene in the alkylation reactor from 1:1 to 30:1 molar, preferably from about 1:1 to 10:1 molar.

When benzene is alkylated with propylene to produce cumene, the preferred catalyst is phosphorus-modified MCM-49 or phosphorus-modified MCM-56. The alkylation reaction is also preferably conducted under liquid phase conditions including a temperature of up to about 250° C., e.g., up to about 150° C., e.g., from about 10° C. to about 125° C.; a pressure of about 250 atmospheres or less, e.g., from about 1 to about 30 atmospheres; and an aromatic hydrocarbon weight hourly space velocity (WHSV) of from about 5 hr$^{-1}$ to about 250 hr$^{-1}$, preferably from 5 hr$^{-1}$ to 50 hr$^{-1}$.

The use of the phosphorus modifier in the alkylation catalyst of the invention is found to enhance the alkylation activity of the catalyst over a wide range of aromatic compound to alkylating agent molar ratios, thereby allowing operation at higher space velocities and hence increasing production capacity. In addition, the presence of the phosphorus is found to increase the selectivity of the catalyst for the production of the desired monoalkylated product and decrease its selectivity for the production of polyalkylated products. Further, the phosphorus modification may increase the hydrothermal stability of the catalyst, thereby enhancing its regenerability.

The alkylation reactor effluent contains the excess aromatic feed, monoalkylated product, polyalkylated products, and various impurities. The aromatic feed is recovered by distillation and recycled to the alkylation reactor. Usually a small bleed is taken from the recycle stream to eliminate unreactive impurities from the loop. The bottoms from the aromatic distillation are further distilled to separate monoalkylated product from polyalkylated products and other heavies.

Additional monoalkylated product may be produced by transalkylation.

The polyalkylated products may be recycled to the alkylation reactor to undergo transalkylation or they may be reacted with additional aromatic feed in a separate reactor. It may be preferred to blend the bottoms from the distillation of monoalkylated product with a stoichiometric excess of the aromatic feed, and react the mixture in a separate reactor over a suitable transalkylation catalyst. The transalkylation catalyst may be a catalyst comprising a zeolite such as MCM-36, MCM-49, MCM-56, MCM-22, PSH-3, SSZ-25, zeolite X, zeolite Y, zeolite beta, or mordenite. Such transalkylation reactions over zeolite beta are disclosed in the aforementioned U.S. Pat. No. 4,891,458; and further such transalkylations using an acid dealuminized mordenite are disclosed in U.S. Pat. No. 5,243,116.

Another particular form of mordenite, which may be used as a transalkylation catalyst, is TEA mordenite, i.e., synthetic mordenite prepared from a reaction mixture comprising a tetraethylammonium directing agent. TEA mordenite is disclosed in U.S. Pat. Nos. 3,766,093 and 3,894,104. The effluent from the transalkylation reactor is blended with alkylation reactor effluent and the combined stream distilled. A bleed may be taken from the polyalkyated product stream to remove unreactive heavies from the loop or the polyalkyated product stream may be distilled to remove heavies prior to transalkylation.

The invention will be described with reference to the following Examples.

EXAMPLE 1

Ethylbenzene Synthesis from Benzene and Ethylene Over Unmodified MCM-22

An MCM-22 catalyst was prepared as a 65/35 extrudate with 65 wt. % MCM-22 crystal with 35 wt% alumina. One gram of the catalyst was charged to an isothermal, well-mixed Parr autoclave reactor along with a mixture comprising of benzene (195 g) and ethylene (20 g). The reaction was carried out at 428° F. and 550 psig for 4 hours. A small sample of the product was withdrawn at regular intervals and analyzed by gas chromatography. The catalyst performance was assessed by a kinetic activity rate constant based on ethylene conversion and by the ethylbenzene selectivity at 100% ethylene conversion. The results for the kinetic activity rate constant are given in Table 1 and for the ethylbenzene selectivity are given in Table 2.

EXAMPLE 2

Ethylbenzene Synthesis from Benzene and Ethylene Over MCM-22 Modified with Phosphorous Impregnated Via Phosphoric Acid ($H_3PO_4$) Solution 0.1-10 grams of $H_3PO_4$ were dissolved in 50 grams of distilled water to yield a solution of pH ranging from 3.1 to 6.9. The resulting solution was used to impregnate fifty grams of a fresh sample of the MCM-22 catalyst used in Example 1 by an incipient wetness method. The impregnated catalyst was dried at 250° F. for 12 hours in air followed by calcination at a temperature between 400 and 1200° F. in flowing air for 4 hours. The resulting phosphorus weight loading varied from 0.5% to 5%. One gram of the final catalyst was evaluated for benzene alkylation with ethylene according to the procedure described in Example 1. Catalyst performance is compared with that of the unmodified MCM-22 of Example 1 in Tables 1 and 2.

EXAMPLE 3

Ethylbenzene Synthesis from Benzene and Ethylene Over MCM-22 Modified with Phosphorous Impregnated Via Dibasic Ammonium Phosphate (($NH_4)_2HPO_4$) Solution 0.1-10 grams of $(NH_4)_2HPO_4$ were dissolved in 50 grams of distilled water to yield a solution of pH ranging from 4.9 to 7.1. The resulting solution was used to impregnate fifty grams of a fresh sample of the MCM-22 catalyst used in Example 1 by an incipient wetness method. The impregnated catalyst was dried at 250° F. for 12 hours in air followed by calcination at a temperature between 400 and 1200° F. in flowing air for 4 hours. The resulting phosphorus weight loading varied from 0.5% to 5%. One gram of the final catalyst was evaluated for benzene alkylation with ethylene according to the procedure described in Example 1. Catalyst performance is compared with that of the unmodified MCM-22 of Example 1 in Tables 1 and 2.

EXAMPLE 4

Comparison of Catalyst Performance

The performance of MCM-22 modified with phosphorous impregnated via an anionic precursor such as phosphoric acid ($H_3PO_4$) or dibasic ammonium phosphate (($NH_4)_2HPO_4$) is compared with unmodified MCM-22 in Tables 1 and 2 below. The data in Table 1 represent kinetic rate constants evaluated based upon ethylene conversion in the autoclave according to the procedure outlined in Example 1. It will be seen from Table 1 that the modification of the MCM-22 with phosphorus increased its activity for benzene alkylation with ethylene by 27% in Example 2 and by 37% in Example 3.

TABLE 1

| | Catalyst | | |
|---|---|---|---|
| | Example 1 | Example 2 | Example 3 |
| Kinetic Rate Constant | 41 | 52 | 56 |

The data in Table 2 represent the ethylbenzene selectivity at 100% ethylene conversion according to the procedure outlined in Example 1. It will be seen from Table 2 that the modification of the MCM-22 with phosphorus increased its selectivity for ethylbenzene production by decreasing its selectivity to diethylbenzene (by 12% in Example 2 and by 18% in Example 3) and by decreasing its selectivity to triethylbenzene (by 14% in Example 2 and by 29% in Example 3).

TABLE 2

| Catalyst | Ethylbenzene (EB) wt. % | DiEB/EB wt. % | TriEB/EB wt. % | Reduction in DiEB, wt. % | Reduction in TriEB, wt. % |
|---|---|---|---|---|---|
| Example 1 | 91.9 | 8.5 | 0.35 | | |
| Example 2 | 92.8 | 7.5 | 0.3 | 11.7 | 14.2 |
| Example 3 | 93.3 | 7 | 0.25 | 17.6 | 28.5 |

EXAMPLE 5

Cumene Synthesis from Benzene and Propylene Over Unmodified MCM-56

MCM-56 catalyst was prepared as a 65/35 extrudate with 65 wt % MCM-56 crystal with 35 wt % alumina. One gram of the catalyst was charged to an isothermal well-mixed Parr autoclave reactor along with a mixture comprising of benzene (156 g) and propylene (28 g). The reaction was carried out at 266° F. and 300 psig for 4 hours. A small sample of the product was withdrawn at regular intervals and analyzed by gas chromatography. The catalyst performance was assessed by a kinetic activity rate constant based on propylene conversion and cumene selectivity at 100% propylene conversion. The results are given in Tables 3 and 4.

EXAMPLE 6

Cumene Synthesis from Benzene and Propylene over MCM-56 Modified with 0.1 wt. % Phosphorus Impregnated Via Phosphoric Acid ($H_3PO_4$) Solution 0.2 grams of $H_3PO_4$ were dissolved in 50 grams of distilled water, and the resulting solution was used to impregnate fifty grams of a fresh sample of the MCM-56 used in Example 5 by an incipient wetness method. The impregnated catalyst was dried at 250° F. for 12 hours in air followed by calcination at 400° F. in flowing air for 4 hours, resulting in 0.1 wt. % P-loading. One gram of the final catalyst was evaluated for benzene alkylation with propylene according to the procedure described in Example 5. Catalyst performance is compared with that of unmodified MCM-56 in Table 3.

EXAMPLE 7

Cumene Synthesis from Benzene and Propylene over MCM-56 Modified with 0.5 wt. % Phosphorus Impregnated Via Phosphoric Acid ($H_3PO_4$) Solution 1.0 grams of $H_3PO_4$ were dissolved in 50 grams of distilled water and the resulting solution was used to impregnate fifty grams of a fresh sample of the MCM-56 used in Example 5 by an incipient wetness method. The impregnated catalyst was dried at 250° F. for 12 hours in air followed by calcination at 400° F. in flowing air for 4 hours, resulting in 0.5 wt. % P-loading. One gram of the final catalyst was evaluated for benzene alkylation with propylene according to the procedure described in Example 5. Catalyst performance is compared with that of unmodified MCM-56 in Table 3.

EXAMPLE 8

Cumene Synthesis from Benzene and Propylene Over MCM-56 Modified with 1.0 wt. % Phosphorus Impregnated Via Phosphoric Acid ($H_3PO_4$) Solution 2.0 grams of $H_3PO_4$ were dissolved in 50 grams of distilled water, and the resulting solution was used to impregnate fifty grams of a fresh sample of MCM-56 used in Example 5 by an incipient wetness method. The impregnated catalyst was dried at 250° F. for 12 hours in air followed by calcination at 400° F. in flowing air for 4 hours, resulting in 1.0 wt. % P-loading. One gram of the final catalyst was evaluated for benzene alkylation with propylene according to the procedure described in Example 5. Catalyst performance is compared with that of unmodified MCM-56 in Table 3.

EXAMPLE 9

Cumene Synthesis from Benzene and Propylene Over MCM-56 Modified with 2.0 wt. % Phosphorus Impregnated Via Phosphoric Acid ($H_3PO_4$) Solution 4.0 grams of $H_3PO_4$ were dissolved in 50 grams of distilled water, and the resulting solution was used to impregnate fifty grams of a fresh sample of MCM-56 used in Example 5 by an incipient wetness method. The impregnated catalyst was dried at 250° F. for 12 hours in air followed by calcination at 400° F. in flowing air for 4 hours, resulting in 2.0 wt. % P-loading. One gram of the final catalyst was evaluated for benzene alkylation with propylene according to the procedure described in Example 5. Catalyst performance is compared with that of unmodified MCM-56 in Table 3.

EXAMPLE 10

Comparison of Catalyst Performance

The performance of MCM-56 modified with phosphorus impregnated via an anionic precursor such as phosphoric acid ($H_3PO_4$) is compared with unmodified MCM-56 in Table 3 below. The data represent kinetic rate constants evaluated based upon propylene conversion as well as cumene selectivity measured as the amount of di-isopropylbenzene formed per unit amount of cumene produced according to the procedure outlined in Example 5. It will be seen from Table 3 that modification of MCM-56 with phosphorus (0.1-0.5 wt. %) increased its activity for the alkylation of benzene with propylene and that modification of MCM-56 with phosphorus (0.1-1 wt. %) increases its selectivity to cumene rather than diisopropylbenzene (DIPB).

TABLE 3

| Catalyst | Kinetic Rate Constant | DiPB/Cumene (wt. %) |
| --- | --- | --- |
| Example 5 | 128 | 16.0 |
| Example 6 | 140 | 13.1 |
| Example 7 | 155 | 13.1 |
| Example 8 | 120 | 14.9 |
| Example 9 | 95 | 17.5 |

EXAMPLE 11

Cumene Synthesis from Benzene and Propylene Over MCM-56 Pretreated Under Hydrothermal Conditions 25 g of the MCM-56 catalyst used in Example 5 were exposed to a 80/20 mixture of steam and air at a GHSV of 300 $h^{-1}$ for 24 hours at 1000° F. One gram of the final catalyst was evaluated for benzene alkylation with propylene according to the procedure described in Example 5, and catalyst performance is described in Table 4.

EXAMPLE 12

Cumene Synthesis from Benzene and Propylene Over Phosphorus-Modified MCM-56 Pretreated Under Hydrothermal Conditions 25 g of finished catalyst from Example 7 was exposed to a 80/20 mixture of steam and air at a GHSV of 300 h$^{-1}$ for 24 hours at 1000° F. One gram of the final catalyst was evaluated for benzene alkylation with propylene according to the procedure described in Example 5, and catalyst performance is described in Table 4.

EXAMPLE 13

Comparison of Catalyst Performance

The performance of MCM-56 modified with phosphorous and steamed is compared with unmodified steamed MCM-56 in Table 4 below. The data represent kinetic rate constants evaluated based upon propylene conversion as well as cumene selectivity measured as the amount of diisopropylbenzene (DIPB) formed per unit amount of cumene produced according to the procedure outlined in Example 5. It will be seen from Table 4 that the phosphorus-modified catalyst of Example 7 exhibited significantly higher stability against hydrothermal deactivation than the unmodified catalyst of Example 5.

TABLE 4

| Catalyst | Kinetic Rate Constant | DiPB/Cumene (wt. %) |
|---|---|---|
| Example 5 | 128 | 16.0 |
| Example 7 | 155 | 13.1 |
| Example 11 | 10 | 26.0 |
| Example 12 | 75 | 18.5 |

The invention claimed is:

1. A process for producing a monoalkylaromatic compound comprising the steps of:
    (a) contacting an alkylation catalyst with mixture of steam and air at a temperature of up to about 1000° F. (538° C.), said alkylation catalyst comprising a porous crystalline inorganic oxide material of MCM-49 and 0.1 to about 0.5 weight percent phosphorous to produce a regenerated alkylation catalyst;
    (b) supplying a reactor with an alkylatabic alkylaromatic compound and an alkylating agent in the presence of said regenerated alkylation catalyst to produce said monoalkylaromatic compound under alkylation conditions;
  wherein said regenerated alkylation catalyst has a higher activity and higher selectivity towards said monoalkylaromatic compound than said regenerated alkylation catalyst that is unmodified by phosphorus under equivalent alkylation conditions.

2. The process of claim 1, wherein said alkylation catalyst has a higher selectivity to cumene than said alkylation catalyst that is unmodified by phosphorus under equivalent alkylation conditions.

3. The process of claim 1, wherein said alkylation catalyst has a higher hydrothermal stability than said alkylation catalyst that is unmodified by phosphorus under equivalent alkylation conditions.

4. The process of claim 2, wherein said alkylation catalyst has a higher hydrothermal stability than said alkylation catalyst that is unmodified by phosphorus under equivalent alkylation conditions.

5. The process of claim 1, wherein the alkylation conditions are such as to maintain the alkylatable aromatic compound substantially in the liquid phase.

6. The process of claim 4, wherein the alkylation conditions are such as to maintain the alkylatable aromatic compound substantially in the liquid phase.

* * * * *